United States Patent
Guo

(10) Patent No.: US 11,788,401 B2
(45) Date of Patent: Oct. 17, 2023

(54) SYSTEMS AND METHODS FOR CHARACTERIZING SUBSURFACE FORMATION PROPERTIES THROUGH GEOCHEMICAL LOGGING

(71) Applicant: ExxonMobil Technology and Engineering Company, Spring, TX (US)

(72) Inventor: Pingjun Guo, Bellaire, TX (US)

(73) Assignee: ExxonMobil Technology and Engineering Company, Spring, TX (US)

(*) Notice: Subject to any disclaimer, the term of this patent is extended or adjusted under 35 U.S.C. 154(b) by 211 days.

(21) Appl. No.: 16/793,313

(22) Filed: Feb. 18, 2020

(65) Prior Publication Data

US 2020/0340352 A1 Oct. 29, 2020

Related U.S. Application Data

(60) Provisional application No. 62/839,120, filed on Apr. 26, 2019.

(51) Int. Cl.
*E21B 49/00* (2006.01)
*E21B 47/003* (2012.01)
(Continued)

(52) U.S. Cl.
CPC .......... *E21B 47/003* (2020.05); *E21B 47/135* (2020.05); *G01V 5/12* (2013.01); *G06F 17/12* (2013.01)

(58) Field of Classification Search
CPC ....... E21B 47/003; E21B 47/135; G01V 5/12; G06F 17/12
See application file for complete search history.

(56) References Cited

U.S. PATENT DOCUMENTS 9,851,468 B2 12/2017 Herron et al.
2010/0258309 A1* 10/2010 Ayodele ............ E21B 36/04
166/272.3
(Continued)

FOREIGN PATENT DOCUMENTS

CA 2678289 A1 * 3/2011 ............ G01V 1/28
CN 104 500 049 A 4/2015
(Continued)

OTHER PUBLICATIONS

Fertl, W.H., et al (1980), "Gamma ray spectral evaluation techniques identify fractured shale reservoirs and source-rock characteristics", Journal of Petroleum Technology, Society of Petroleum Engineers, Nov. 1980, pp. 2053-2062.
(Continued)

*Primary Examiner* — Kyle R Quigley
*Assistant Examiner* — Christine Y Liao
(74) *Attorney, Agent, or Firm* — ExxonMobil Technology and Engineering Company—Law Department

(57) ABSTRACT

Systems and methods relating to determination of oil saturation, kerogen content, and/or water saturation within kerogen-containing subsurface formations such as unconventional formations (e.g., tight formations such as shales) are provided herein. These methods advantageously rely on a simplified measurement process, reducing the direct measurements of a subsurface formation relied upon in determining oil saturation, kerogen content, and/or water saturation. In particular, methods according to some embodiments include determining or otherwise obtaining values of TOC; bulk density; porosity; and densities of kerogen, oil, and water corresponding to a subsurface formation of interest or a zone thereof. Methods of various embodiments further include, based at least in part upon the obtained values, determining one or more of kerogen content, oil saturation (Continued)

Source rock petrophysical model $S_o$, and water saturation $S_w$ of the subsurface formation of interest, and/or a corresponding zone thereof.

16 Claims, 2 Drawing Sheets

(51) Int. Cl.
  *E21B 47/135* (2012.01)
  *G01V 5/12* (2006.01)
  *G06F 17/12* (2006.01)

(56) References Cited

U.S. PATENT DOCUMENTS

| | | | |
|---|---|---|---|
| 2015/0094960 A1 | 4/2015 | Viswanathan et al. | |
| 2017/0218752 A1* | 8/2017 | Donderici | E21B 47/113 |
| 2017/0248011 A1* | 8/2017 | Craddock | G01N 33/241 |
| 2018/0149768 A1 | 5/2018 | Guo et al. | |
| 2020/0332654 A1* | 10/2020 | Rowe | E21B 21/065 |

FOREIGN PATENT DOCUMENTS

| | | | |
|---|---|---|---|
| WO | 2016007400 A1 | 1/2016 | |
| WO | WO-2017083059 A1 * | 5/2017 | G01V 3/32 |

OTHER PUBLICATIONS

Passey, Q.R., et al. (1990), "A practical model for organic richness from porosity and resistivity logs", The American Assoc of Petroleum Geologists Bulletin, vol. 74, Dec. 1990, pp. 1777-1794.

Schmoker, J.W., et al. (1982/1983), "Organic carbon in Bakken formation, United States portion of Williston Basin", The American Assoc of Petroleum Geologists Bulletin, vol. 67 (No. 12), manuscript accepted Mar. 1983, pp. 2165-2174.

Zhao et al. (2007) "Thermal maturity of the Barnett Shale determined from well-log analysis", AAPG Bulletin, vol. 91, No. 4 (Apr. 2007), pp. 535-549.

* cited by examiner

SYSTEMS AND METHODS FOR CHARACTERIZING SUBSURFACE FORMATION PROPERTIES THROUGH GEOCHEMICAL LOGGING

CROSS-REFERENCE TO RELATED APPLICATION

This application claims the benefit of U.S. Provisional Application 62/839,120, filed Apr. 26, 2019, entitled Systems and Methods for Characterizing Subsurface Formation Properties Through Geochemical Logging, the entirety of which is incorporated by reference herein.

TECHNOLOGICAL FIELD

Exemplary embodiments described herein pertain to the production of oil or gas (hydrocarbons) and geophysical prospecting. More specifically, exemplary embodiments described herein pertain to systems and methods for characterizing subsurface formation properties such as hydrocarbon saturation using geochemical logging data and/or techniques, and managing hydrocarbons based upon such characterizations.

BACKGROUND

This section is intended to introduce various aspects of the art, which may be associated with exemplary embodiments of the present technological advancement. This discussion is believed to assist in providing a framework to facilitate a better understanding of particular aspects of the technological advancement. Accordingly, it should be understood that this section should be read in this light, and not necessarily as admissions of prior art.

Accurate quantification of hydrocarbon saturation and volumes in a subsurface formation of interest play an important role in characterizing a hydrocarbon reservoir in the subsurface formation, and furthermore in informing hydrocarbon management decisions with respect to the subsurface formation. Well logs provide continuous records of rock properties recorded along the wellbore using logging tools either during (logging-while-drilling or LWD) or after well drilling operations (wireline logging). Log data may provide physical measurements responding to formation bulk density and porosity, conductivity and resistivity, sonic wave travel times, and bound and mobile fluid contents; and such data are often used in petrophysical evaluation to characterize rock and fluid properties along the wellbore. For instance, reservoir pore space and pore fluid fractions may be derived from such petrophysical analysis.

Traditional petrophysical evaluation methods rely primarily on resistivity logs and the Archie model (which empirically correlates resistivity log with water saturation in the formation) in estimating formation fluid saturation. In particular, the Archie model assumes water is the only electrically conductive medium in the formation, such that water saturation can be computed from the measured porosity and resistivity logs when water salinity is known. Water saturation $S_w$ is defined as the fraction of pore space filled with water; its complement is hydrocarbon saturation $S_o$ (that is, the entirety of pore space is assumed filled by either water or hydrocarbon, such that any pore volume not filled with water is assumed filled with hydrocarbon). Porosity is defined as the total pore volume per unit rock volume and is a measurement of potential hydrocarbon volume within reservoir rock in a subsurface formation. Porosity and water saturation (and hydrocarbon saturation) are important parameters in characterizing a subsurface formation and/or making hydrocarbon management decisions regarding the formation.

The Archie models in conjunction with resistivity and porosity logs have been successfully applied to obtain these important characteristics in conventional reservoirs, where reservoir rock and fluid properties are relatively homogeneous and don't show significant variations within reservoir intervals.

Further, more recently, U.S. Pat. No. 9,851,468 describes another approach to determining hydrocarbon saturation in conventional reservoirs: deriving total organic carbon (TOC) values from geochemical logging tools, and calibrating TOC to hydrocarbon saturation.

Examples of geochemical logging tools such as those referenced in the '468 Patent include neutron spectroscopy tools which operate by emitting neutrons into the subsurface formation, thereby inducing gamma ray-generating reactions in atoms of the various elements constituting the subsurface formation, and recording or otherwise capturing the emitted gamma rays, which are characteristic of the elemental composition of the formation. These tools enable measuring elemental carbon contents (and other elemental contents, such as Si, Ti, S, Ca, Fe, etc.) of the subsurface formation, but further processing is required to distinguish between inorganic or mineral carbon, and organic carbon (e.g., TOC). Thus, post-processing methods (e.g., for converting measured elemental concentrations to mineral concentrations) may be utilized to characterize the concentrations of carbon-containing minerals (e.g., carbonates), so as to subtract out such minerals' contributions and obtain the TOC value from the geochemical log. See, for example, U.S. Patent Publication No. 2018/0149768, the contents of which are incorporated herein by reference, describing a method in which elemental concentrations are normalized to dry matrix weights first and are then subsequently combined to form mineral compounds to describe formation matrix mineral composition.

However, there are many challenges in applying the above techniques in subsurface formations comprising unconventional hydrocarbon reservoirs (which may also be referred to as shale, tight oil, and/or source rock reservoirs). Such shale reservoirs typically comprise stacked source rocks with high degrees of heterogeneity in rock properties. Resistivity tool response is suppressed because of the excessive conductivity of source rocks or shale. With the assumption of non-conductive rock matrix, for instance, conventional Archie model-based techniques would calculate too high a water saturation (i.e., it would erroneously attribute rock conductivity to water conductivity, assuming too great a water content). The characteristics of tight source rock reservoirs such as low porosity and complex pore structures also make it difficult to establish Archie models for accurate petrophysical evaluation, because Archie model parameters are also strongly impacted by the complex pore structures and wettability of source rocks. Varying formation water salinity or resistivity profiles in source rocks also lead to large uncertainties in Archie water saturation models.

Furthermore, the geochemical logging-based method of the '468 Patent for calibrating TOC to hydrocarbon saturation in conventional formations would also not work in unconventional formations. This is because unconventional source-rock formations contain large amounts of kerogen, the organic remnants of ancient life preserved in sedimentary rocks under temperature and pressure that have undergone (and/or are undergoing) thermal maturation processes to generate hydrocarbons. Unlike conventional reservoirs where hydrocarbon accumulates after migrating out of source rocks, source rock reservoirs act as both hydrocarbon sources and reservoirs. And, key to the present disclosure, they contain substantial amounts of kerogen.

Geochemical logs and associated processing methods for determining TOC do not distinguish between carbon signal from kerogen, and carbon signal from hydrocarbons. (In addition to the '468 Patent, see also, e.g., the Delta Log R method (Passey et al., 1990), which can indicate the presence of high TOC rocks; the Schmoker method (Schmoker and Hester, 1983), which correlates bulk density log to TOC volumes using core data; and the uranium method (Fertl and Ricke, 1980), which relies on the assumption that uranium content in source rocks is proportional to TOC volume.) Accordingly, one cannot accurately determine hydrocarbon saturation from TOC in unconventional reservoirs using currently known methods. Therefore, between these issues and the problems associated with resistivity logs in unconventional formations, determining oil saturation in unconventional formations remains a complex task. Current methods often rely on cumbersome direct measurements of oil saturation, and/or calibration using core sample analysis and an extensive calibration database, and/or measurements of formation water resistivity and/or dielectric logs to determine oil saturation in these situations. Furthermore, the applicability of core-calibrated saturation models is limited to wells in which the core calibration database is originated and is not recommended in non-cored wells in heterogonous mud rock reservoirs where rock types and lithofacies often vary across wells.

Other references of potential interest include U.S. Pat. Nos. 8,311,744; 9,851,468; 9,310,513; 2015/0094960; 2015/0260034; 2016/0266275; and 2018/0149768.

It would be desirable to have a more straightforward, less costly, and less error-prone method for determining hydrocarbon saturation in unconventional reservoirs, to avoid the need for excessive different collection activities that add expense and complication to reservoir characterization processes, and furthermore can introduce significant compounding errors into the final hydrocarbon saturation determination.

SUMMARY

The present inventor has recognized a new way to determine oil saturation $S_o$ of a subsurface formation of interest using geochemical logging measurements in combination with known, easily measured, or easily referenced characteristics of the subsurface formation, while solving the problem of distinguishing between kerogen and hydrocarbon in total organic carbon (TOC) determinations. In particular, methods according to some embodiments include determining or otherwise obtaining values of TOC; bulk density; porosity; and densities of kerogen, oil, and water corresponding to a subsurface formation of interest or a zone thereof. Methods of various embodiments further include, based at least in part upon the obtained values, determining one or more of kerogen content, oil saturation $S_o$, and water saturation $S_w$ of the subsurface formation of interest, and/or a corresponding zone thereof. Advantageously, such methods may in some embodiments allow determination of $S_o$ and/or $S_w$ without the need to use core sample analysis/calibration specifically targeted to the subsurface formation of interest, and/or without the need to obtain resistivity and/or dielectric measurements of the subsurface formation of interest.

Presently described methods in various embodiments may further include utilizing these outputs to characterize the subsurface formation of interest and/or to make/execute hydrocarbon management decisions regarding such subsurface formation.

BRIEF DESCRIPTION OF THE DRAWINGS

While the present disclosure is susceptible to various modifications and alternative forms, specific example embodiments thereof have been shown in the drawings and are herein described in detail. It should be understood, however, that the description herein of specific example embodiments is not intended to limit the disclosure to the particular forms disclosed herein, but on the contrary, this disclosure is to cover all modifications and equivalents as defined by the appended claims. It should also be understood that the drawings are not necessarily to scale, emphasis instead being placed upon clearly illustrating principles of exemplary embodiments of the present invention. Moreover, certain dimensions may be exaggerated to help visually convey such principles.

DETAILED DESCRIPTION

Figure 1:
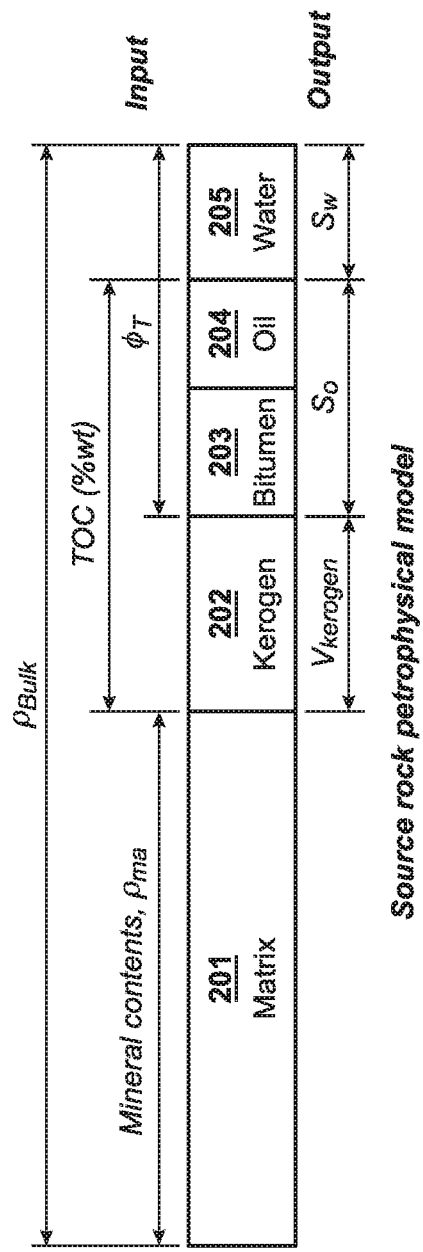
FIG. 1 shows a conceptual model illustrating constituents of a subsurface formation or zone thereof.

Exemplary embodiments are described herein. However, to the extent that the following description is specific to a particular embodiment, this is intended to be for exemplary purposes only and simply provides a description of the exemplary embodiments. Accordingly, the invention is not limited to the specific embodiments described below, but rather, it includes all alternatives, modifications, and equivalents falling within the true spirit and scope of the appended claims.

The presently described methods in various embodiments provide a simplified approach to characterizing a kerogen-containing subsurface formation of interest and/or making hydrocarbon management decisions based upon such characterization. In particular, various embodiments described herein leverage in a new way the recognition of an important feature of kerogen-containing subsurface formations: that kerogen density is fairly constant across a known subsurface region (e.g., a basin), and therefore reference to kerogen density determined for a different portion of the subsurface region (e.g., logs or core samples obtained from previously drilled wells in the subsurface region) may be used as a substantially accurate proxy for kerogen density in a subsurface formation of interest within the subsurface region. This, combined with readily obtained values of oil and/or water density for a given subsurface formation of interest, helps solve the dilemma described above, wherein kerogen contribution cannot readily be removed from a TOC measurement in kerogen-containing (e.g., unconventional) formations. Reference herein to "kerogen-containing" is meant to include subsurface formations with a substantial amount of kerogen, that is, such that kerogen content as compared to hydrocarbon content is non-negligible, This phenomenon is explained in more detail with reference to Rudnicki, M., *Variation of organic matter density with thermal maturity*, AAPG BULLETIN v. 100, No. 1 (January 2016), pp. 17-22. As discussed therein (and illustrated, e.g., in FIG. 2 of that reference), Kerogen density does not vary substantially over a range of Kerogen maturity corresponding to vitrinite reflectance % Ro between about 0.5% and 5.0%. See also Waters, C. C., H. Freund, S. R. Keleman, P. Peczak, and D. J. Curry, *Predicting oil and gas compositional yields via chemical structure-chemical yields modeling (CS-CYM): Part 2-Application under laboratory and geologic conditions*, ORGANIC GEOCHEMISTRY, v. 38, pp. 306-322 (2007). Of particular interest for purposes of the present disclosure, such kerogen maturity range also corresponds to kerogen maturity within the oil-generating windows of time. Once Ro exceeds about 5%, the source rock is over-mature and the reservoirs containing such over-mature kerogen are well in the gas-generating windows.

The presently disclosed methods for the first time take advantage of the relatively constant kerogen density in subsurface formations containing kerogen of maturity within the oil-generating window, such that kerogen density can be assumed known for a subsurface formation of interest based on reference to other kerogen density measurements from a subsurface region containing the subsurface formation (typically, kerogen density values are published and/or otherwise known for a given subsurface region such as a basin).

This recognition, in combination with other relatively straightforward density measurements as described herein, enables one for the first time to identify and discount kerogen contribution to measured TOC of a subsurface formation of interest, leaving a direct correlation between TOC and oil saturation even in unconventional (tight oil) formations such as shale. Such methods can advantageously avoid the need for complex or error-prone measurements conventionally used to devise oil saturation, such as resistivity or dielectric measurements of formation water; core sampling and calibration with other oil saturation values from the subsurface region containing the subsurface formation of interest. (Further, as noted previously, the applicability of core-calibrated saturation models is limited to wells in which the core calibration database is originated, and is not recommended in non-cored wells in heterogonous mud rock reservoirs where rock types and lithofacies often vary across wells.

Accordingly, methods of various embodiments include: (a) determining organic carbon content, mineral volumes, and matrix density $\rho_{ma}$ of the subsurface formation of interest (and/or of a zone thereof); (b) determining porosity of the subsurface formation of interest (and/or a zone thereof); (c) obtaining a bulk density value of the subsurface formation or interest (and/or a zone thereof); and (d) obtaining additional density values (comprising oil density, water density, and kerogen density) of the subsurface formation of interest (and/or a zone thereof) (again noting, per the above, that such density values can advantageously be obtained for a given subsurface formation of interest from other portions of the subsurface region containing the subsurface formation). The method further includes, based on the obtained or estimated values (a)-(c), determining oil saturation $S_o$, water saturation $S_w$, and/or kerogen volume ($V_{kero}$) of the subsurface formation and/or zone thereof. In general, the obtained measurement and other values may equivalently be referred to as "inputs" and the oil saturation $S_o$, water saturation $S_w$ and/or kerogen volume ($V_{kero}$) as "outputs," and in particular embodiments, determination of such outputs is made utilizing a petrophysical model (and in particular, a multivariable petrophysical model). All or part of the determinations and/or obtaining of estimates may be carried out, as explained in more detail below, by computer processor(s) taking as input data, information, or other measurements obtained from the subsurface formation of interest.

FIG. 1 provides a conceptual model illustrating constituents of a subsurface formation or zone thereof—noting that a "zone" in this description refers to a portion of the subsurface formation along a path, such as a wellbore, penetrating or otherwise traversing the subsurface formation (a "zone" may also be referred to as a measured depth (MD) interval, although this is not intended to refer solely to depth, as a zone may be found along a partially or wholly horizontal portion of a borehole in a horizontal well). FIG. 1 shows the above-noted inputs and outputs, and their correspondence to the various constituents of the subsurface formation or zone thereof: (the matrix (or non-hydrocarbon, non-water mineral composition) of the subsurface formation 201; kerogen 202; bitumen 203; oil 204; and formation water 205, with the bitumen and oil together forming the hydrocarbon content (wherein "oil" as used in this model may include both liquid and gaseous hydrocarbons). The ordinarily skilled artisan will appreciate that some or all of the constituents described in FIG. 1 and elsewhere herein may require measurement and/or determination on a zone-by-zone basis, depending upon the subsurface region (e.g., basin) or formation of particular interest. For instance, in some subsurface regions, such as the Delaware Basin, properties such as non-water mineral composition may vary greatly from zone to zone. And while an "averaged" value for mineral constituency and/or other properties may be applied across multiple zones or an entire subsurface formation (e.g., along an entire wellbore), the ordinarily skilled artisan will recognize where zone-to-zone variations are great enough that such an "averaged" value may not provide adequate accuracy, in which case inputs may be obtained (and/or outputs determined) on a zone-by-zone basis. In yet other circumstances, variations among different zones may admit of the use of averaged values of inputs (and/or the calculation of averaged outputs) across the entire subsurface formation of interest. The present methods are applicable to both zone-by-zone calculation and/or formation-wide calculation.

Each of these aforementioned aspects of methods according to various embodiments will be described in more detail below.

Obtaining Inputs

According to some embodiments, the following inputs may be obtained (see also the labeled "Inputs" along the top of the conceptual model illustration of FIG. 1), generally in any order (regardless of which order they are discussed herein), unless context clearly indicates otherwise.

The first inputs of interest are formation TOC, mineral constituent volume fractions or weight fractions or quantities, and matrix density $\rho_{ma}$ of the subsurface formation of interest (and/or of a zone thereof). Unless otherwise noted, such volume and/or weight fractions are on the basis of the entire volume (or weight) of the mineral contents within the subsurface formation of interest. With reference to FIG. 1, these three inputs (TOC wt %, mineral volume or weight fraction, matrix density $\rho_{ma}$), may, according to some embodiments, advantageously be obtained through a single geochemical logging procedure, e.g., by deploying a geochemical logging tool into the subsurface formation. Deployment may be by any suitable means, including via logging-while-drilling (LWD) geochemical logging tools deploying during drilling of a borehole into the subsurface formation of interest, or wireline geochemical logging tools deployed into the drilled borehole. Thus, methods according to some embodiments include obtaining geochemical logging data from a subsurface formation of interest (and/or zone(s) thereof), and determining, based on the geochemical logging data, TOC, mineral constituent quantities (e.g., weight, volume, concentration), and matrix density of the subsurface formation (and/or zone(s) thereof).

Suitable geochemical logging tools may comprise a neutron source and one or more gamma ray detectors. This type of neutron source is capable of producing high energy neutrons that are capable of inducing inelastic scattering interactions with colliding with elements such as carbon atoms and releasing inelastic gamma rays in addition to capture gamma rays. An example of these high energy neutron sources is the DT pulsed neutron source currently used in pulsed neutron logging tools. The deuterium and tritium (DT) reaction produces a 14 MeV neutron and a helium atom after a high speed deuterium ion beam striking a tritium target. The neutron source emits neutrons into the subsurface formation, which interact with nuclei of the various elements in the subsurface formation to generate characteristic gamma rays (such rays having unique energies for elements in the formation). The gamma ray detector(s) is/are capable of detecting the so-generated gamma rays and recording gamma ray counts as a function of gamma ray energy. Preferably, the detector(s) detect both fast neutron inelastic and thermal neutron capture reactions from elements in the subsurface formation, resulting from the neutron emission into the formation. The recorded gamma ray spectrum (which may be referred to as a geochemical spectroscopy log or a geochemical log) accordingly contains information of elemental concentrations within the subsurface formation (e.g., formation concentrations of one or more of carbon, silicon, calcium, sulfur, titanium, potassium, sodium, nickel, copper, etc.). The recorded data may provide such concentrations on a zone-by-zone basis within the subsurface formation, although concentrations may also or instead be determined for the formation generally rather than zone-by-zone.

The spectroscopy data from recorded gamma rays may be interpreted (whether zone-by-zone, for one or more zones, or for the entirety of the subsurface formation of interest) using suitable known spectral decomposition or other post-processing techniques to invert or otherwise solve for elemental yields and weight fractions, providing measurements of elemental concentrations to describe elemental constituents in the subsurface formation of interest (or one or more zones thereof). Further post-processing may be used to determine formation mineral (as opposed to elemental) concentration or composition, generally based upon the elemental concentration(s). For example, U.S. Pat. No. 8,311,744 describes examples of such post-processing of geochemical log data to determine elemental concentrations, and then the use of a classifier or classification system to take elemental concentrations as input and provide lithotypes as output (enabling determination of mineral concentrations). U.S. Patent Publication No. 2018/0149768 provides another, different, example of post-processing methods for quantifying mineral compositions and concentrations from geochemical log data. U.S. Pat. No. 9,851,468 also discusses this conversion, at col. 3.

There are other empirical methods to interpret minerals from elemental concentrations using empirical relationships derived from core X-ray diffraction (XRD) and X-ray fluorescence (XRF) database. The mathematical correlations or regression models are simple to use but become less accurate when a large distance away from either the wells or deposition environments where the core data were collected. (Herron, S. L. and Herron, M. M., 1996, Quantitative lithology: an application for open and cased hole spectroscopy, SPWLA 37$^{th}$ Annual Logging Symposium, June 16-19). XRD analysis is a non-destructive method to measure mineral composition, in which an x-ray beam is directed at a rock sample and the scattered x-ray spectrum is analyzed as a function of scatter angle to provide mineral composition information. XRF analysis is another non-destructive method using x-ray beams to measure rock chemical composition in terms of elemental concentration by analyzing the induced x-ray energy spectrum as a function of energy. There are less commonly used analysis techniques for rock samples including Fourier transform infrared spectroscopy utilizing infrared radiation and micro-Raman method utilizing laser and optical microscope.

Other suitable methods for converting from elemental to mineral compositions may include, e.g., the use of inelastic (capture) spectrum, which is the sum of the inelastic (capture) spectra for individual elements weighted by their concentrations. The elemental concentrations can be determined by doing a least-squares fit of standard elemental spectra to the measured spectrum. The resulting weighting coefficients are called relative spectral or elemental yields. The important elements for inelastic spectroscopy are carbon (C), oxygen (O), calcium (Ca), silicon (Si), sulfur (S), iron (Fe), and aluminum (Al), magnesium (Mg). The important elements for capture spectroscopy are hydrogen (H), chlorine (Cl), silicon (Si), calcium (Ca), sulfur, (S), iron (Fe), gadolinium (Gd), titanium (Ti), aluminum (Al), magnesium (Mg). Elemental weight fractions of dry rock matrix are calculated from the relative spectral yields and the spectral sensitivity factors which are tool design dependent and are calibrated parameters using laboratory rock standards. In the mineral calibration process, oxides closure models are applied at each logging depth to relate elemental weight fractions with common mineralogical associations such as CaO and SiO2. Oxygen concentration is not a required input as it is difficult to partition oxygen between matrix, borehole, and pore fluids. Inelastic spectroscopy analysis provides unique measurements of magnesium (Mg), aluminum (Al), carbon (C), and oxygen (0) which are important elements in quantifying dolomite, clay minerals and total organic carbon (TOC). Integration of elemental weight fractions that are common in inelastic and capture spectroscopy data is performed to improve measurement accuracy. These common elements are calcium (Ca), silicon (Si), sulfur (S), and iron (Fe). Mineral weight interpretation is carried out by either sequential or inversion methods. Linear regression models as described by Herron and Herron (1996) are a sequential method to predict mineralogy using elemental weight fractions with mathematical correlations derived from a core data base. The multi-mineral solver formulation entails that geochemical and conventional logs are combined to form a set of log response equations with matrix mineral concentrations and pore fluid volumes as unknowns. End member properties of matrix components and fluids as well as log responses are preferably known or assumed. A linear inversion solver is applied to solve for mineral concentrations and fluid saturations. The process is often iterated manually to achieve convergence criteria (Galford J. et al., 2009, field test results of a new neutron-induced gamma-ray spectroscopy geochemical logging tool, SPE 123992, the SPE Annual Technical Conference and Exhibition, New Orleans, La., September 24-27; Colson, J. L., et al., 1989, applications using geochemical logs, SPE 17963, the SPE Middle East Oil Technical Conference and Exhibition, Manama, Bahrain, March 11-14).

In US Patent Application, 20180149768, the present inventor also disclosed a new field-specific inversion method to interpret and quantify mineral compositions and concentrations by building mineral composition models from a non-linear inversion of core or log elemental and mineral concentration data. One key advantage of this method is that the mineral composition models are uniquely defined using core XRD and XRF data in a specific field or reservoir and accuracy of mineral concentrations is greatly improved when applying the mineral composition models in the geochemical log interpretation. Other methods rely on global core databases (e.g., those developed by oilfield service providers and the like) and default mineral composition, and often lead to inaccurate mineral concentrations in heterogeneous mud rock reservoirs.

Such tools may be used to generate geochemical spectroscopy logs, enabling determination, zone-by-zone (and/or for the entire subsurface formation of interest), of dry-weight (e.g., exclusive of formation water) element concentrations, matrix density, mineral volume/weight fractions, and TOC.

Thus, a suitable geochemical logging process for obtaining geochemical logging data, including TOC, may include emitting a plurality of neutrons into a subsurface formation (and/or into a zone thereof), thereby inducing emission of gamma rays from elements in the subsurface formation (and/or zone thereof), and detecting the emitted gamma rays. The emitted and detected gamma rays preferably include both those induced by inelastic scattering of the emitted neutrons, and those induced by thermal capture reactions of the emitted neutrons. Emission may be via a neutron source and detection may take place using a gamma-ray detector. Such processes preferably (but not necessarily) employ a geochemical logging tool comprising both the neutron source and gamma-ray detector. The process for obtaining TOC continues with post-processing or similar determination process based on the detected gamma rays to obtain, e.g., values of mineral concentrations, matrix density $\rho_{ma}$, and carbon content (in wt %) of the subsurface formation. That is, some methods may include determining (by post-processing or otherwise), based on the detected gamma rays, values of mineral concentrations, matrix density $\rho_{ma}$, and carbon content of the subsurface formation and/or zone(s) thereof. Such determination may take place by a processor (e.g., a CPU as described below in connection with FIG. 2 or any other computer processor or the like). The processor may include associated memory (RAM, ROM, or some other non-transitory computer readable medium) for storing data corresponding to detected gamma rays and/or data corresponding to determined values of mineral concentrations, matrix density $\rho_{ma}$, and carbon content of the subsurface formation and/or zone(s) thereof. In certain embodiments, the processor and/or associated non-transitory computer readable medium may be a processor of the geochemical logging tool. In other embodiments, data may be transferred from a geochemical logging tool to another computer system (such as computer system 2400 described below in connection with FIG. 2).

Determining or otherwise obtaining TOC values of the subsurface formation (or zone thereof) may further comprise correcting the determined carbon content (e.g., determined based on the geochemical logging data, such as detected gamma rays) to eliminate contributions from (a) inorganic carbon (e.g., carbon-containing rocks of the subsurface formation or zone thereof, such as carbonates), and (b) organic carbons in oil-based drilling mud, e.g., in the wellbore (or portion of the wellbore corresponding to the zone from which the geochemical log is obtained), so as to obtain a corrected TOC value. This corrected TOC therefore represents the organic carbon content in the formation or zone thereof (e.g., with reference to FIG. 1, kerogen, bitumen, and oil), and may be used as the TOC value obtained from the subsurface formation or zone thereof in workflows of various.

Inorganic or mineral carbon may be removed from the initial TOC value by any suitable means. For example, with reference to post-processing techniques from which mineral concentrations are obtained (see discussion above for some examples), the mineral concentration of carbonate or other carbon-containing rocks in the subsurface formation may be used to determine inorganic carbon content for subtraction from the elemental carbon wt % derived directly from the geochemical log's TOC measurements. Similarly, drilling mud's organic carbon contribution may be removed by reference to the quantity of drilling mud introduced into the borehole or portion thereof corresponding to the zone(s) in the subsurface formation from which the geochemical logging data is obtained. Quantifying drilling mud in this manner may be done by any suitable means, e.g., by mass balance principles and monitoring input flow as to the total drilling mud introduced into the borehole or portion thereof (with appropriate reference to the concentration of carbon in such quantity of drilling mud). Or, one may simply use a plurality of TOC log measurements from a corresponding plurality of zones of the subsurface formation. For example, one may select a TOC measurement from one or more zones (depth intervals) where there is no or very little carbon in the formation such as wet sands, and then use the TOC signal in such zone(s) as the borehole mud TOC background (that is, the contribution to TOC log measurements from the drilling mud). Borehole diameter or caliper may also be used/referenced to account for the borehole size variations (e.g., by fitting the mud TOC signal as a function of borehole diameter). Other suitable methods for correcting TOC log measurements for drilling mud carbon contents will be apparent to the skilled artisan with the benefit of this disclosure.

TOC measurements or values may be obtained in units of wt % or weight fraction, relative to the mass of dry-weight matrix components (e.g., exclusive of water and of the TOC itself (oil, bitumen, kerogen).

As noted above, the same geochemical logging procedure may advantageously include obtaining mineral concentration (e.g., in weight fraction and/or volume fraction), and matrix density $\rho_{ma}$ of the subsurface formation of interest (and/or of one or more zones thereof), in addition to the above-described TOC value(s). For instance, the post-processing or other determination of mineral contents (e.g., based on detected gamma rays) may also include determination of mineral constituent volumes and/or matrix density (e.g., according to methods such as those previously described above). Furthermore, determination of mineral contents also may enable characterization of the lithology of the formation (or zone(s) thereof), so as to obtain matrix or grain density by reference to known density values based upon the mineral constituents (e.g., based upon the determined quantities of carbonates, shales, sandstones, limestones, calcites, and other mineral constituents).

For instance, matrix density $\rho_{ma}$ may be calculated from mineral weight fractions and mineral density according to Equation (1):

$$\frac{1}{\rho_{ma}} = \sum_{i=1}^{m} \frac{w_i}{\rho_i} \quad (1)$$

where $w_i$ and $\rho_i$ is weight fraction and density of the ith mineral.

With reference back to FIG. 1, further inputs of interest (in addition to the just-discussed (a) organic carbon content, mineral volumes, and matrix density $\rho_{ma}$) include: (b) porosity $\Phi_t$ of the subsurface formation of interest and/or zone(s) thereof. Thus, methods of some embodiments further comprise (b) obtaining porosity value(s) of the subsurface formation and/or zone(s) thereof. Porosity may be obtained through any suitable means known to the skilled artisan. For example, a total porosity log may be obtained, e.g., through obtaining data of the subsurface formation through nuclear magnetic resonance (NMR) log and based on the NMR data, calculating or otherwise determining porosity. Using NMR for porosity determinations may in many instances be much better than use of NMR for other log measurements; NMR is not as error-prone in the context of porosity determination as it is in other contexts.

As another example, matrix density of the formation and/or zone(s) thereof (determined, e.g., per above description) may be used in combination with bulk density (discussed below) to obtain a total porosity log, by applying an assumption of fluid density(ies) in the zone or formation of interest and solving for the quantity of fluid (assumed to occupy the corresponding pore space of the matrix) indicated by the difference between matrix and bulk densities. Fluid density(ies), e.g., of oil and water of the subsurface formation, may be assumed or obtained as discussed below. According to some embodiments, where porosity is so-determined from bulk density (which may be referred to as determining porosity using a density porosity model), some such density porosity models may not account for kerogen's contribution to density in the non-porous matrix. A simple iteration (one, two, or if necessary more) can be carried out once kerogen volume fraction is computed per the present methods—to refine the porosity calculation, and in turn update the kerogen computation based on the refined porosity calculation, with iteration until a match (or near-match) in porosity and/or kerogen values from one iteration to the next. In certain embodiments wherein porosity is determined using a density porosity model, an "initial guess" of porosity may advantageously be obtained from porosity measured from a core sample.

With further reference back to FIG. 1, an additional input according to some embodiments includes bulk density $\rho_{bulk}$ of the subsurface formation and/or zone(s) thereof, and methods according to such embodiments therefore further include (c) obtaining a bulk density value of the formation and/or zone(s) thereof. This input may be obtained from bulk density logs and/or core analysis or fluid analysis, e.g., according to conventional means known to those of skill in the art. For instance, fluid densities can be measured directly from a core sample or fluid sample obtained at a given depth or zone. Since density will be a function of temperature and pressure, one can extrapolate from the measured fluid densities to determine fluid densities along the entire wellbore, given temperature and pressure measurements from the zone of interest along the wellbore. Bulk density is then of course obtained from the determined fluid density and the already-determined matrix density (see above discussion).

The bulk density value may, in certain embodiments, be determined (e.g., by a processor or otherwise) based upon such bulk density log and/or core analysis from the subsurface formation of interest (and/or zone(s) thereof). Suitable processors for this determination are in line with those discussed in connection with determining TOC, mineral contents, and matrix density (e.g., a processor (optionally with associated non-transitory computer readable media) that is contained and/or otherwise associated with a logging tool or core analysis system; or a processor (optionally with associated non-transitory computer readable media) of a separate computer system 2400 per FIG. 2).

Methods according to various embodiments further comprise (d) obtaining additional density values (comprising water density $\rho_w$, oil density $\rho_o$, and kerogen density $\rho_{kero}$) for the subsurface formation (and/or zone(s) thereof). These additional density values may be obtained by any suitable means, although according to particular embodiments, they are advantageously obtained through reference to density measurements, logs, core analysis or other records of a subsurface region comprising the subsurface formation of interest, or of a subsurface formation having similar lithology to the subsurface formation of present interest. Such measurement values may be referred to as "representative values" of kerogen density, oil density, and/or water density. Advantageously, such representative values may have been acquired for the subsurface region before or otherwise independently from drilling and/or other hydrocarbon management activities related to the specific subsurface formation of interest (e.g., from core sampling, logging, or other measurements obtained from drilling, logging, and/or other activities associated with a location (e.g., a different well) of the subsurface region different from the subsurface formation of present interest). For example, representative oil and water densities may be available from reservoir fluid analysis using either downhole or produced fluid samples (e.g., measured directly from fluid samples taken using downhole fluid sampling tools such as wireline or LWD tools, or from surface-produced fluid samples taken at a wellhead), and/or regional databases associated with the subsurface region containing the subsurface formation of interest. Representative kerogen densities may be available from core samples or other analysis or measurements obtained from the subsurface region. As discussed above in connection with determining bulk density, fluid densities may be correlated for applicability at various zones along a wellbore, based upon the temperature and pressure at each zone of interest. Kerogen densities similarly may be calibrated for correspondence to a given zone along the wellbore, as kerogen density likewise is a function of temperature and pressure.

Also or instead, these values may be obtained by reference to calibration, correlation, or other comparison to known values, e.g., in a database or the like; for instance, reference may be to known reference properties (e.g., for kerogen density generally and/or oil and/or water density, generally). For instance, water and/or oil density may be referenced according to commonly available regional catalog values of water density at given temperature and pressure, and/or assumed for. (Note that these methods may also be suitable for measuring fluid densities in connection with some options for bulk density determination as discussed above.) For some discussion of reference water density as a function of temperature and pressure, for example, see Log INTERPRETATION CHARTS, Schlumberger (2009 ed.), at p. 9 (illustrating in situ water density values for given T and P).

Methods in accordance with particular embodiments therefore advantageously may omit core sampling, logging, or other measurement activity of the subsurface formation of interest related to obtaining kerogen density, oil density, or water density, in favor of reliance on already-measured representative values (e.g., from other wells or other areas within the subsurface region in which the subsurface formation of interest is located). Or, methods according to some embodiments may omit logging or core sampling in a particular zone of interest, and/or multiple zones of interest, relying on a single core sample taken from the subsurface formation of interest (especially from a different zone along a wellbore penetrating that subsurface formation).

Furthermore, methods in accordance with various of these and other embodiments may omit resistivity and/or dielectric logs or other resistivity and/or dielectric measurement processes. That is, according to such embodiments, no measurement of resistivity and/or dielectric properties of the subsurface formation of interest take place in determination of the output(s). Similarly, in these and other embodiments, no NMR log or similar measurement takes place in connection with determining the output(s) for the subsurface formation of interest (and/or zone(s) thereof). Further, in these or other embodiments, determination of any of the outputs (discussed below) may take place without obtaining or analyzing core samples in connection with such determination. In particular embodiments, determinations may be made for a particular zone (or zones) of the subsurface formation, potentially using NMR and/or core sampling from a different zone of the subsurface formation—but requiring no NMR and/or core sampling associated with the zone(s) for which determination of outputs (e.g., oil saturation, water saturation, and/or kerogen volume fraction) is made.

As explained above, such methods are adequately able to supply the kerogen, oil, and/or water density values useful in various of the present methods, because of the recognition that kerogen density is fairly constant and typically well known for a given subsurface formation (e.g., based on reference to the subsurface region containing such formation).

The present methods take particular advantage of the inventor's recognition that these parameters (kerogen, oil, and water densities) have low levels of sensitivity in log data. That is, representative values of kerogen density, oil density, and water density can be obtained for the subsurface region, using core data, other regional reservoir studies, regional databases, and the like (e.g., such representative values are not obtained from core samples, logs, and/or other measurement techniques applied to the particular subsurface formation of interest). Moreover, note that there is sufficient density contrast between oil density and kerogen density such that the present methods can accurately solve for both of those values with a high degree of confidence in the accuracy of the determined outputs. For instance, typical kerogen densities, particularly in the kerogen maturity window of interest (see discussion above), are within the range of about 1.25 to about 1.75 g/cm$^3$. Typical oil densities, on the other hand, are within the range of about 0.80 to about 0.95 g/cm$^3$. The density contrast provides sufficient dynamic sensitivity to quantify kerogen and oil using log measurements (e.g., the geochemical log measurements discussed). In these ways, among others, the present methods differ from conventional practices, which try to solve all these density parameters using a limited number of wellbore log measurements of the subsurface formation of interest.

Determining Outputs

Methods according to various embodiments further comprise determining, based upon the previously described inputs, oil saturation, water saturation, and/or kerogen volume of the subsurface formation of interest (and/or zone(s) thereof). Such determination of one or more of these outputs may be carried out using a processor (which may be the same or a different processor from the processor(s) carrying out calculations or other determinations of the various inputs based on measured quantities of the subsurface formation) following code or other executable instructions embedded in a non-transitory computer-readable medium (e.g., RAM, ROM, or other computer memory) associated with the processor.

For instance, recognizing the fact that kerogen and fluid properties do not vary significantly within the areas of interest within mature source rock regions, it is possible to formulate optimized workflows and algorithms to solve for the output parameters as shown in FIG. 1. Thus, the determination of outputs according to some embodiments may include solving a system of two or more modeling equations. For instance, according to some embodiments, this may be a system of equations built using mass balance principles and/or other physical principles linking log response and reservoir properties. Advantageously, according to some embodiments, this may be a system of linear equations. One such example is shown below in the system of equations (1)-(4).

$$\rho_b = (1-\emptyset_t - V_{kero})^* \rho_{ma} + V_{kero}^* \rho_{kero}°\emptyset_t^* S_o^* \rho_o + \emptyset_t^*(1-S_o)^* \rho_w \quad (1)$$

$$TOC = TOC_{kero} + TOC_o \quad (2)$$

$$TOC_{kero}^* \rho_{ma}^*(1-\emptyset_t) = V_{kero}^* \rho_{kero}^* C_{kero} \quad (3)$$

$$TOC_o^* \rho_{ma}^*(1-\emptyset_t) = S_o^* \rho_o^* C_o^* \emptyset_t \quad (4)$$

In the system of equations (1)-(4), TOC, $\rho_b$, $\rho_{ma}$, $\emptyset_t$ are input parameters for TOC weight % or weight fraction (on the basis of dry matrix weight), bulk density (g/cm$^3$), grain density (g/cm$^3$), and porosity (volume fraction or volume percent), respectively. $S_o$, $V_{kero}$, $TOC_{kero}$, $TOC_o$ are output parameters for oil saturation (volume fraction or percent), kerogen volume (as volume fraction or percent), kerogen TOC weight fraction, and oil TOC weight fraction, respectively. It is also noted that $S_w$ is replaced by the term $(1-S_o)$, in recognition that $S_w + S_o = 1$. Known average or representative values of kerogen and reservoir fluid properties (e.g., oil density, water density) are used for kerogen density $\rho_{kero}$, oil density $\rho_o$, formation water density $\rho_w$. Similarly, known average or representative values are used for carbon weight fraction of kerogen $C_{kero}$, and carbon weight fraction of oil $C_o$. Carbon weight fraction is calculated as ratio of carbon weight to hydrocarbon molecular weight, and is typically obtained from lab analysis of a fluid sample (e.g., indicating the relative fraction of different constituents, such as $C_1$, $C_2$, $C_3$, . . . $C_x$ hydrocarbons in the crude oil and/or gas). For example, carbon weight fraction of oil made of single CH2 molecules moieties is 12.011/(12.011+2*1.008)=0.85, where carbon molecular weight is 12.011 and hydrogen molecular weight is 1.008. Hydrocarbon liquids normally have multiple carbon components and the carbon weight fraction is a weight sum of various carbon compounds. In the exploration stage of an oil field, the carbon weight data are obtained as part of the geochemical analysis of reservoir fluid samples which are essential data for reservoir engineering analysis and simulation in field exploration and development. Kerogen carbon weight quantification uses known pyrolysis methods such as Rock-Eval on organic matter samples that are extracted from core.

More generally, in this and related implementations, the inputs may be in accordance with any of the above-described inputs (e.g., TOC and matrix density from neutron spectroscopy logs, bulk density and porosity log).

The relative simplicity of the above-described method and variants thereof can be illustrated by comparison to U.S. Patent Publication No. 2015/0094960 (mentioned also in the Background section above). That document describes multiple saturation logs to compute oil saturation: starting with TOC log (e.g., via geochemical logging) to provide a TOC measurement, then introducing NMR to provide total fluid saturation including oil and water, then continuing with a water saturation measurement using dielectric or resistivity logs, followed by obtaining oil saturation by subtracting dielectric or resistivity based water saturation from NMR total fluid saturation. Moreover, kerogen or organic matter volume is not computed in that method.

Methods for Post-Processing, Calculations, and Other Determinations

Determining the outputs may take place using a processor, such as a CPU. Such processor may be, e.g., a CPU associated with a computer system, such as computer system 2400 as shown in FIG. 2.

Figure 2:
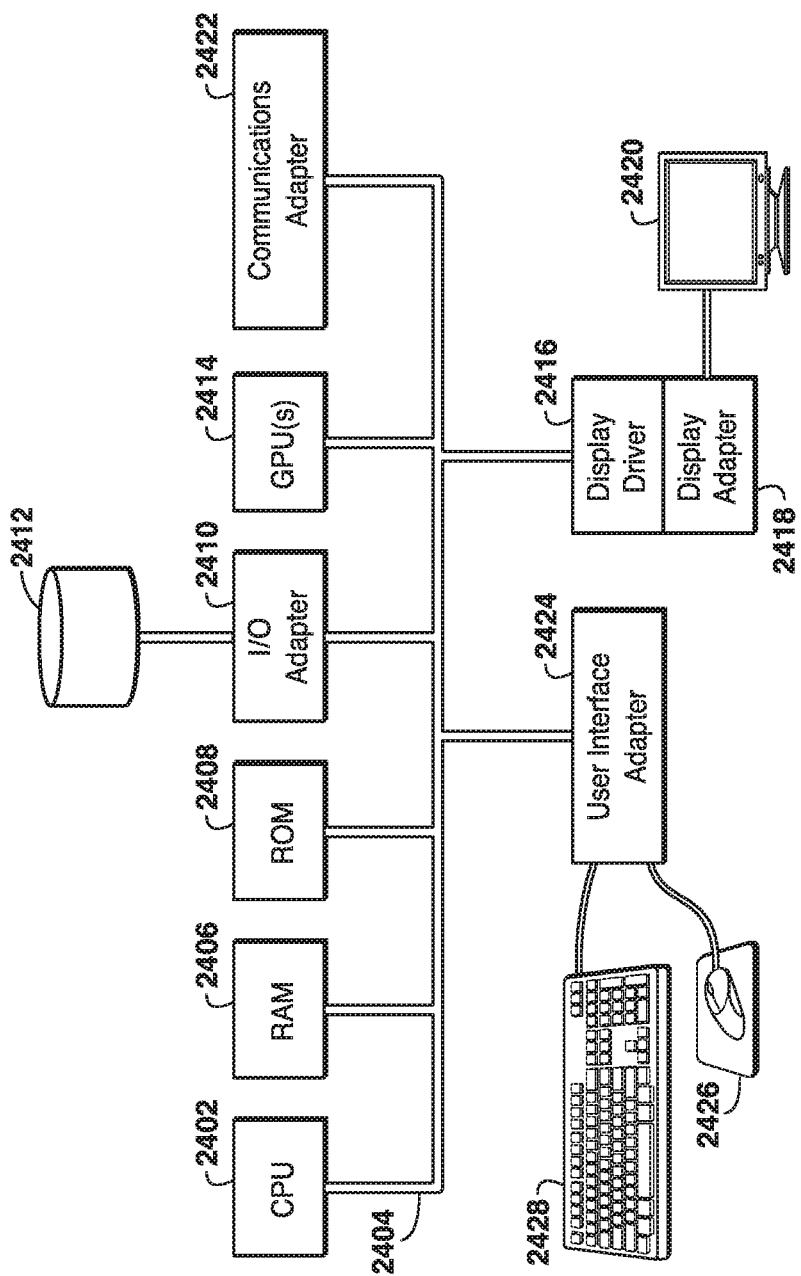
FIG. 2 illustrates a computer system and components thereof which may be useful in connection with carrying out various methods described herein.

FIG. 2 is a block diagram of a computer system 2400 that can be used to execute some or all of the present techniques. A central processing unit (CPU) 2402 is coupled to system bus 2404. The CPU 2402 may be any general-purpose CPU, although other types of architectures of CPU 2402 (or other components of exemplary system 2400) may be used as long as CPU 2402 (and other components of system 2400) supports the operations as described herein. Those of ordinary skill in the art will appreciate that, while only a single CPU 2402 is shown in FIG. 2, additional CPUs may be present. Moreover, the computer system 2400 may comprise a networked, multi-processor computer system that may include a hybrid parallel CPU/GPU system. The CPU 402 may execute the various logical instructions according to various teachings disclosed herein. For example, the CPU 2402 may execute machine-level instructions for performing processing and/or other determination according to the above description with respect to determining any one or more outputs, and/or with respect to determining any one or more of the various inputs (e.g., determining mineral concentration, matrix density, and/or TOC based on detected gamma rays as described above).

The computer system 2400 (and other computer systems and/or processors as discussed herein) may also include or be associated with computer components such as nontransitory, computer-readable media. Examples of computer-readable media include a random access memory (RAM) 2406, which may be SRAM, DRAM, SDRAM, or the like. The computer system 2400 may also include, and/or a processor may be associated with, additional non-transitory, computer-readable media such as a read-only memory (ROM) 2408, which may be PROM, EPROM, EEPROM, or the like. RAM 2406 and ROM 2408 hold user and system data and programs, as is known in the art. The computer system 2400 may also include, and/or a processor may be associated with, an input/output (I/O) adapter 2410, a communications adapter 2422, a user interface adapter 2424, one or more graphics processing nits (GPUs) 2414, and/or one or more display adapters 2418. One or more display drivers 2416 may contain computer-readable code or other similar instructions to convert computer-readable information into visual images on the display adaptor 2418. In particular embodiments in which a logging tool such as a geochemical logging tool comprises a processor, it may also comprise some or all of these components of computer system 2400 associated with such processor.

The I/O adapter 2410 may connect additional non-transitory, computer-readable media such as a storage device(s) 2412, including, for example, a hard drive, a compact disc (CD) drive, a floppy disk drive, a tape drive, and the like to computer system 2400. The storage device(s) may be used when RAM 2406 is insufficient for the memory requirements associated with storing data for operations of the present techniques. The data storage of the computer system 2400 may be used for storing information and/or other data used or generated as disclosed herein. For example, storage device(s) 2412 may be used to store configuration information or additional plug-ins in accordance with the present techniques. Further, user interface adapter 2424 couples user input devices, such as a keyboard 2428, a pointing device 2426 and/or output devices to the computer system 400. The display adapter 2418 is driven by the CPU 2402 to control the display on a display device 2420 to, for example, present information to the user regarding available plug-ins.

The architecture of system 2400 may be varied as desired. For example, any suitable processor-based device may be used, including without limitation personal computers, laptop computers, computer workstations, and multi-processor servers. Moreover, the present technological advancement may be implemented on application specific integrated circuits (ASICs) or very large scale integrated (VLSI) circuits. In fact, persons of ordinary skill in the art may use any number of suitable hardware structures capable of executing logical operations according to the present technological advancement. The term "processing circuit" encompasses a hardware processor (such as those found in the hardware devices noted above), ASICs, and VLSI circuits. Input data to the computer system 2400 may include various plug-ins and library files. Input data may additionally include configuration information.

Characterizing Subsurface Formations and Managing Hydrocarbons

In various embodiments, oil saturation, water saturation, and/or kerogen volume of the subsurface formation and/or zone(s) thereof (and in particular embodiments, oil saturation), is/are further employed in characterizing the subsurface formation of interest. For example, methods may further include employing the thus-determined oil saturation (and/or water saturation or kerogen volume) in hydrocarbon management activities (e.g., methods may further include managing hydrocarbons based on the determined oil saturation (and/or determined water saturation and/or kerogen volume)). Oil saturation, as determined by the present methods, includes in situ bitumen (or heavy oil), light oil, and gas (see FIG. 1 for correspondence between $S_o$ and oil and bitumen in the illustrative model).

As used herein, "hydrocarbon management" or "managing hydrocarbons" includes any one or more of the following: hydrocarbon extraction; hydrocarbon production, (e.g., drilling a well and prospecting for, and/or producing, hydrocarbons using the well; and/or, causing a well to be drilled to prospect for hydrocarbons); hydrocarbon exploration; identifying potential hydrocarbon-bearing formations; characterizing hydrocarbon-bearing formations; identifying well locations; determining well injection rates; determining well extraction rates; identifying reservoir connectivity; acquiring, disposing of, and/or abandoning hydrocarbon resources;

reviewing prior hydrocarbon management decisions; and any other hydrocarbon-related acts or activities. The aforementioned broadly include not only the acts themselves (e.g., extraction, production, drilling a well, etc.), but also or instead the direction and/or causation of such acts (e.g., causing hydrocarbons to be extracted, causing hydrocarbons to be produced, causing a well to be drilled, causing the prospecting of hydrocarbons, etc.).

As a particular example of hydrocarbon management, methods may include, based on the determined oil saturation (and/or water saturation and/or kerogen volume) resource density assessments for the subsurface formation of interest and/or a region (e.g., a basin) containing the subsurface formation; oil in place (OIP) and reserves estimation; drill well planning; sweet spot identification to geosteer or land lateral or horizontal wells in unconventional (tight oil) formations such as shale (e.g., drilling a well to a location within the subsurface formation based at least in part on the determined oil saturation); as well as in guiding well completion, e.g., guiding hydraulic fracturing operations (such as in determining fraccing intervals). These characterizations may further guide hydrocarbon management activities (e.g., executing the aforementioned fracturing operations, drilling a well or causing a well to be drilled in the subsurface formation of interest based upon the determined oil saturation, and/or making other hydrocarbon management decisions).

Further, As used herein, "obtaining" data, measurements, or other information generally refers to any method or combination of methods of acquiring, collecting, or accessing information, including, for example, directly measuring or sensing a physical property, receiving transmitted data, selecting data from a group of physical sensors, identifying data in a data record, generating models from assemblages of data, generating data or models from computer simulations, retrieving data or models from one or more libraries, and any combination thereof.

The present technological advancement has been successfully benchmarked using multiple sets of core data as well as geochemical logs collected from wells in source rock reservoirs of mixed marine siliciclastic and carbonate deposition environments. The mineralogical composition of the stacked organic rich reservoirs is highly variable with relatively high TOC concentration up to 8% by weight. The targeted reservoirs are of high oil saturation. With the knowledge of well characterized properties of reservoir fluids and kerogen the new method was blind tested first and the results were validated with core data. The computed kerogen weight fractions are in good agreement with core pyrolysis data. The computed oil saturation are also in good agreement with Dean-Stark analysis of core plugs. The results are significantly better than existing methods.

The present techniques may be susceptible to various modifications and alternative forms, and the examples discussed above have been shown only by way of example. However, the present techniques are not intended to be limited to the particular examples disclosed herein. Indeed, the present techniques include all alternatives, modifications, and equivalents falling within the spirit and scope of the appended claims.

What is claimed is:
1. A method comprising:
(a) obtaining geochemical logging data from a kerogen-containing subsurface formation of interest or a zone thereof and determining, based on the geochemical logging data, TOC, mineral constituent quantities, and matrix density $\rho_{ma}$ of the subsurface formation or zone thereof;
(b) obtaining porosity of the subsurface formation or zone thereof;
(c) obtaining bulk density of the subsurface formation or zone thereof;
(d) obtaining representative values of kerogen density, oil density, and water density of a subsurface region comprising the subsurface formation from a collected source of regional data, the representative values associated with a location of the subsurface region different from the subsurface formation or zone thereof, and not from measurement techniques applied to the subsurface formation or zone thereof; and
(e) determining one or more of (1) kerogen volume fraction $V_{kero}$, (2) water saturation $S_w$, and (3) oil saturation $S_o$ of the subsurface formation or zone thereof, based upon the TOC, mineral constituent quantities, matrix density, porosity, bulk density, and representative values, by identifying and discounting kerogen contribution to TOC, leaving a direct correlation between TOC and oil saturation $S_o$, and
(f) based upon the determined kerogen volume fraction, water saturation Sw, and/or oil saturation So, managing hydrocarbons in the subsurface formation or zone thereof, wherein managing hydrocarbons comprises carrying out or causing to be carried out one or more well completion activities in the subsurface formation based at least in part on the determined oil saturation.

2. The method of claim 1, wherein (a) obtaining geochemical logging data comprises (a1) using a geochemical logging tool, emitting a plurality of neutrons into the subsurface formation or zone thereof, thereby inducing emission of gamma rays from elements in the subsurface formation or zone thereof, and (a2) using the geochemical logging tool, detecting the emitted gamma rays, and further wherein the geochemical logging data comprises the detected gamma rays.

3. The method of claim 2, wherein determining TOC, mineral constituent quantities, and matrix density $\rho_{ma}$ of the subsurface formation or zone thereof is carried out by a processor of the geochemical logging tool.

4. The method of claim 1, wherein determining TOC of the subsurface formation or zone thereof comprises correcting a determined carbon content determined based on the geochemical logging data to eliminate contributions from (i) inorganic carbon and (ii) organic carbons in oil-based drilling mud, so as to obtain a corrected TOC value to be used as the determined TOC.

5. The method of claim 1, wherein (b) obtaining porosity comprises obtaining data of the subsurface formation or zone thereof through nuclear magnetic resonance (NMR) logging, and based on the NMR data, determining porosity.

6. The method of claim 1, wherein (b) obtaining porosity comprises determining the porosity value based on the determined matrix density of the subsurface formation or zone thereof and determined bulk density of the subsurface formation or zone thereof.

7. The method of claim 1, wherein the representative values of kerogen density, oil density, and/or water density are determined from a regional database associated with the subsurface region.

8. The method of claim 1, wherein no measurement of resistivity and/or dielectric properties of the subsurface formation of interest take place in connection with the determination of kerogen volume fraction $V_{kero}$, water saturation $S_w$, and/or oil saturation $S_o$ of the subsurface formation or zone thereof.

9. The method of claim 1, wherein no NMR logging measurement takes place in connection with the determination of kerogen volume fraction $V_{kero}$, water saturation $S_w$, and/or oil saturation $S_o$ of the subsurface formation or zone thereof.

10. The method claim 9, wherein kerogen volume fraction $V_{kero}$, water saturation $S_w$, and/or oil saturation $S_o$ are determined for a zone of the subsurface formation, and further wherein no NMR logging measurement associated with said zone takes place in connection with said determination.

11. The method of claim 1, wherein no core samples are analyzed in connection with the determination of oil saturation $S_o$ of the subsurface formation or zone thereof.

12. The method of claim 1, wherein the determining (e) comprises determining all of kerogen volume fraction $V_{kero}$, water saturation $S_w$, and oil saturation $S_o$ of the subsurface formation or zone thereof.

13. The method of claim 12, wherein the determining (e) comprises determining oil saturation $S_o$ using the following system of equations (1)-(4):

$$\rho_b = (1-\varnothing_t-V_{kero})*\rho_{ma}+V_{kero}*\rho_{kero}°\varnothing_t*S_o*\rho_o+\varnothing_t*(1-S_o)*\rho_w \quad (1)$$

$$TOC = TOC_{kero} + TOC_o \quad (2)$$

$$TOC_{kero}*\rho_{ma}*(1-\varnothing_t) = V_{kero}*\rho_{kero}*C_{kero} \quad (3)$$

$$TOC_o*\rho_{ma}*(1-\varnothing_t) = S_o*\rho_o*C_o*\varnothing_t \quad (4)$$

wherein
- TOC, $\rho_b$, $\rho_{ma}$, $\varnothing_t$ are TOC (in wt % on the basis of dry weight matrix), bulk density, matrix density, and porosity, respectively, of the subsurface formation or zone thereof;
- $S_o$, $V_{kero}$, $TOC_{kero}$, $TOC_o$ are oil saturation volume fraction, kerogen volume fraction, kerogen TOC weight fraction, and oil TOC weight fraction, respectively, of the subsurface formation or zone thereof;
- $\rho_{kero}$, $\rho_o$, and $\rho_w$ are densities of kerogen, oil, and water, respectively, in the subsurface region containing the subsurface formation; and
- $C_{kero}$ and $C_o$ are carbon weight fractions of kerogen and oil, respectively.

14. The method of claim 1, wherein determining (e) comprises solving a system of two or more modeling equations built using mass balance principles and/or other physical principles linking log response and reservoir properties.

15. The method of claim 1, wherein managing hydrocarbons comprises prospecting for hydrocarbons in the subsurface formation based at least in part on the determined oil saturation.

16. The method of claim 1, wherein managing hydrocarbons comprises drilling a well to a location within the subsurface formation based at least in part on the determined oil saturation.

* * * * *